United States Patent [19]

Takeda et al.

[11] 4,261,904

[45] Apr. 14, 1981

[54] TETRAHYDROFURANOL DERIVATIVE

[75] Inventors: Makoto Takeda; Hiroshi Iwane, both of Ami; Takashi Hashimoto, Tokyo, all of Japan

[73] Assignee: Mitsubishi Petrochemical Co., Ltd., Tokyo, Japan

[21] Appl. No.: 68,288

[22] Filed: Aug. 20, 1979

[30] Foreign Application Priority Data

Aug. 18, 1978 [JP] Japan ............... 53-100653

[51] Int. Cl.³ .......................................... C07D 307/20
[52] U.S. Cl. .............................. 260/347.8; 252/522 R
[58] Field of Search ..................................... 260/347.8

[56] References Cited

U.S. PATENT DOCUMENTS 3,978,092 8/1976 Ichikawa et al. ................. 260/347.8

OTHER PUBLICATIONS

Botteghi et al., *J. Org. Chem.*, vol. 37, (1972), pp. 1835–1837.
Johnston et al., J. Org. Chem., vol. 41, (1976), pp. 2611–2614.

*Primary Examiner*—Richard Raymond

*Attorney, Agent, or Firm*—Sughrue, Rothwell, Mion, Zinn and Macpeak

[57] ABSTRACT

A tetrahydrofuranol compound of the general formula:

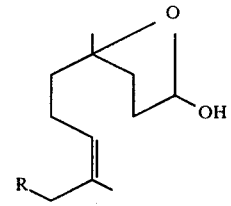

wherein R is H or

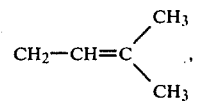

or tautomer thereof; and a method for preparing the same.

3 Claims, No Drawings

TETRAHYDROFURANOL DERIVATIVE

BACKGROUND OF THE INVENTION

1. Field of the Invention

This invention relates to a novel tetrahydrofuranol derivative, a method of producing the same and a perfume containing the same.

2. Description of the Prior Art

No examples of hydroformylation of linalool and nerolidol have heretofore been known in the art. *J. Org. Chem.*, 1972, 37, 1835–1837 teaches production of 2-substituted allyl alcohol wherein the hydroformylation product of an allyl alcohol derivative is subjected to an intramolecular cyclization reaction to form a hemiacetal according to the reaction scheme shown below.

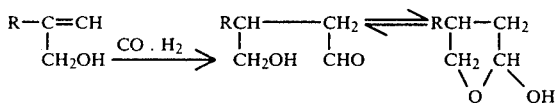

wherein R is a sec-butyl, a tert-butyl or a methyl group.

SUMMARY OF THE INVENTION

One subject of this invention is to provide a tetrahydrofuranol derivative which is useful as a perfume component.

Another object of this invention is to provide a method of producing a tetrahydrofuranol derivative.

A further object of this invention is to provide a perfume containing a tetrahydrofuranol derivative as an effective odoriferous ingredient.

DETAILED DESCRIPTION OF THE INVENTION

The compound according to this invention is a tetrahydrofuranol derivative of the general formula (I):

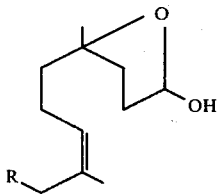

wherein R is H or

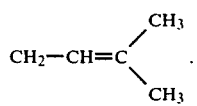

This compound is an aromatic substance which gives off distinctive fragrance that is reminiscent of a mild and natural flower.

The compound is prepared by reacting linalool or nerolidol with carbon monoxide and hydrogen in the presence of a catalyst. The catalyst used is a rhodium compound or cobalt compound. Of these, a rhodium compound is preferred.

Representative examples of the rhodium catalyst used in this invention are complexes wherein rhodium is surrounded by a ligand such as a halide, oxide, carboxylate, nitrate, phosphine, amine, olefin, carbon monoxide or hydrogen. Specific examples of the complex are $RhX_3$, $Rh_2O_3$, $[Rh(OCOCH_3)_2]_2$, $Rh(NO_3)_3$, $Rh_6(CO)_{16}$, $[RhX(CO)_2]_2$, $RhX_3(C_5H_5N)_3$, $[RhX(C_8H_{12})]_2$, $Rh(acac)_3$, $RhX(PR_3)_3$, $RhX(CO)(PR_3)_2$ and $RhH(CO)(PR_3)_3$, wherein X is Cl, Br or I; R is an aliphatic group having 1 to 10 carbon atoms or an aromatic group having 6 to 12 carbon atoms. These rhodium catalysts are commercially available. Those which are relatively easily obtained are $RhCl_3$, $Rh_2O_3$, $Rh(NO_3)_3$ and $RhCl(PPh_3)_3$. Preferred for the reaction are $Rh_2O_3$, $Rh_6(C)_{16}$, $[RhCl(CO)_2]_2$, $RhCl(PPh_3)_3$, $[RhCl(C_8H_{12})]_2$, $RhCl(CO)(PPh_3)_2$ and $RhH(CO)(PPh_3)_3$, and of these $RhH(COZ)(PR_3)_3$ is particularly advantageous. These rhodium compounds may be used as a homogeneous catalyst or as a heterogeneous catalyst in which they are supported on a porous solid carrier such as activated carbon, alumina or silica.

Suitable examples of the cobalt compound used as a catalyst in this invention are Raney cobalt, $Co_2(CO)_8$ and $[(PR_3)Co(CO)_3]_2$, wherein R is an aliphatic group having 1 to 10 carbon atoms or an aromatic group having 6 to 12 carbon atoms. Raney Co and $Co_2(CO)_8$ are commercially available.

A suitable amount of the rhodium catalyst used in this invention is from about $1\times10^{-1}$ to $1\times10^{-6}$ mol, preferably from about $1\times10^{-2}$ to $1\times10^{-5}$ mol, per mol of linalool or nerolidol. A suitable amount of the cobalt catalyst used in this invention is from about $1\times10^{-1}$ to $1\times10^{-4}$ mol, preferably from about $1\times10^{-2}$ to $1\times10^{-3}$ mol, per mol of linalool or nerolidol.

While either catalyst may be used individually, it is understood that for the purpose of inhibiting its decomposition and reducing the reaction pressure, about 1 to $10^3$ mols, preferably about 10 to $10^2$ mols, of a tertiary phosphine may be added to 1 mol of the catalyst. Representative examples of tertiary phosphines are triethyl phosphine, tripropyl phosphine, tributyl phosphine, triphenyl phosphine, trinaphthyl phosphine, tritoluyl phosphine, trinitrophosphine, trichlorophosphine, trimethoxyphenyl phosphine and the like.

The reaction for producing the desired compound of this invention is carried out at a temperature of from about 40° to 150° C., preferably from about 70° to 130° C. The mixing ratio of carbon monoxide to hydrogen is about 0.5:1 to 2:1, preferably about 0.8:1 to 1.2:1 by mol. The reaction is carried out at a pressure of from about 1 to 200 kg/cm², preferably from about 20 to 150 kg/cm².

Examples of the solvent which may be used in the reaction include hydrocarbons such as hexane, heptane, benzene, toluene and xylene; ethers such as tetrahydrofuran, dioxane and dimethylethylene glycol; and chlorinated hydrocarbons such as chlorobenzene and chloroform. Generally linalool and nerolidol are used in these solvents in concentrations of about 10 to 100 vol%, preferably about 20 to 50 vol%, based on the volume of the reactants. If desired, the reaction may be carried out in the absence of such solvents.

The reaction product of this invention is purified by isolation from the reaction mixture through distillation or other conventional purification techniques.

In the general formula (I), where R is hydrogen, the compound is 5-methyl-5-(4-methyl-3-pentenyl)tetrahydro-2-furanol and it is prepared by the following reaction.

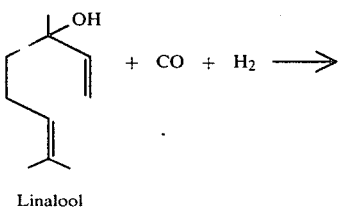

Linalool

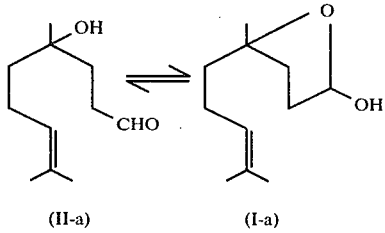

(II-a)　　　　　(I-a)

As is apparent from the above, hydroformylation produces the intermediate (II-a), 4-hydroxy-4,8-dimethyl-7-nonenal, which is subjected to a rapid intramolecular cyclization reaction to form the product (I-a), 5-methyl-5-(4-methyl-3-pentenyl)tetrahydro-2-furanol. The products (I-a) and (II-a) are tautomers for each other, but the forward reaction predominates over the reverse reaction, and the equilibrium composition ratio of (I-a) to (II-a) is 9:1 or more.

Further, where R is

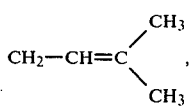

the compound is 5-(4,8-dimethyl-3,7-nonadienyl)-5-methyltetrahydro-2-furanol and it is prepared by the following reaction.

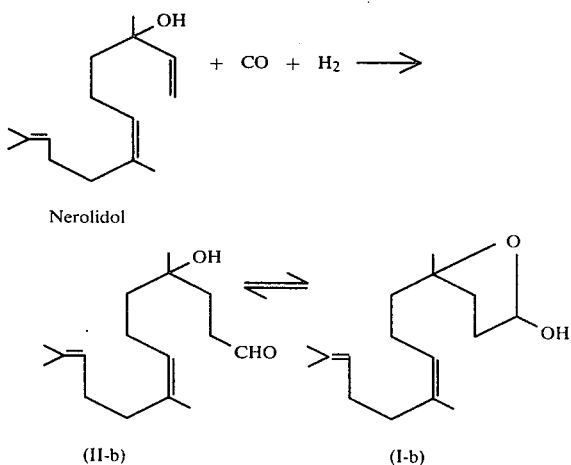

Nerolidol (II-b)　　　　　(I-b)

As is apparent from the above, hydroformylation produces the intermediate (II-b), 4-hydroxy-4,8,12-trimethyl-7,11-tridecadienal, which is subjected to a rapid intramolecular cyclization to form the product (I-b), 5-(4,8-dimethyl-3,7-nonadienyl)-5-methyltetrahydro-2-furanol. The products (I-b) and (II-b) are tautomers for each other, but the forward reaction predominates over the reverse reaction, and the equilibrium composition ratio of (I-b) to (II-b) is 9:1 or more. While the above reaction is illustrated with cis-nerolidol the reaction is also effective with the trans isomer.

The compound of this invention provides a perfume having closer resemblance to the fragrance of natural flowers than any prior art synthetic perfumes, and it may be used alone or in combination with natural perfumes or other synthetic perfumes or with conventional additives employed in perfumery. In most perfume compositions the compound can be used in amounts of about 5 to 100% by weight based on the weight of the perfume. The perfume thus prepared from the compound of this invention is incorporated in aromatic products such as soaps, deodorizers, toilet preparations, cleansers and propellants.

The method of producing the compound of this invention will now be described in greater detail by reference to the following examples. Unless otherwise indicated, all percentages, parts, ratios and the like are by weight.

EXAMPLE 1

A 5-liter Inconel 600 autoclave was charged with 710 g of linalool, 4.5 g of tris(triphenylphosphine)hydridecarbonyl rhodium, 2.6 g of triphenylphosphine and 2.3 liters of toluene. The autoclave was then charged with equal volumes of a mixed gas of carbon monoxide and hydrogen to pressurize the autoclave to 80 kg/cm$^2$. The reaction was carried out at a temperature of 80° C. and at a pressure of 80 to 85 kg/cm$^2$ for 2 hours.

After cooling, the pressure was returned to atmospheric pressure, and the reaction mixture was recovered from the autoclave and distilled for purification to yield 664 g of the reaction product having a boiling point of 93° to 100° C. to 0.7 mmHg. The product consisted of two components:
(1) 5-methyl-5-(4-methyl-3-pentenyl)tetrahydro-2-furanol; and
(2) 4-hydroxy-4,8-dimethyl-7-nonenal.

The ratio of the components (1) to (2) was 95:5.

The NMR spectra of components (1) and (2) had the following absorption characteristics (solvent: CDCl$_3$, TMS as the internal standard):

For both isomers (1) and (2):
 $\delta=1.16$ (s), $\delta=1.40$ (s), $\delta=1.62$ (bs), $\delta=1.70$ (bs), $\delta=1.1$–2.3 (m), $\delta=4.24$ (m), $\delta=5.16$ (m)
For isomer (1): $\delta=5.55$ (m)
For isomer (2): $\delta=2.23$–2.8 (m), $\delta=10.17$ (m)
(s=singlet, bs=broad singlet, m=multiplet).

The reaction product had a distinctive fragrance similar to that of a gardenia.

EXAMPLE 2

A 100 ml Hastelloy C autoclave was charged with 10 g of linalool, 0.44 g of dicobalt octacarbonyl and 25 ml of toluene. The autoclave was then charged with equal volumes of a mixed gas of carbon monoxide and hydrogen to pressurize the autoclave to 120 kg/cm$^2$. The reaction was carried out at a temperature of 110° C. and at a pressure of 100–120 kg/cm$^2$ for 5.5 hours. After cooling, the pressure was returned to atmospheric pressure, and the reaction mixture was recovered from the autoclave and distilled for purification to yield 1.3 g of the reaction product having a boiling point of 111° to 120° C. at 2.0 mmHg. The product consisted of components (1) and (2) in a ratio by mol of 91:9.

EXAMPLE 3

A perfume for use in a toilet preparation was prepared in accordance with the following formulation.

|  | parts |
| --- | --- |
| Benzyl acetate | 100 |
| Benzyl alcohol | 100 |
| α-Amylcinnamic aldehyde | 150 |
| Phenethyl alcohol | 100 |
| β-Ionone | 100 |
| Dihydroisojasmone | 50 |
| Musk ambrette | 50 |
| Vetiver oil | 30 |
| Patchouli oil | 20 |
| Compound (1) | 300 |
|  | 1,000 |

Addition of compound (1) provided the perfume with the sweet smell of a natural flower.

EXAMPLE 4

A 5-liter Inconel 600 autoclave was charged with 410 g of nerolidol, 1.7 g of tris(triphenylphosphine)hydridecarbonyl rhodium, 5.0 g of triphenylphosphine and 2.3 liters of toluene. The autoclave was then charged with equal volumes of a mixed gas of carbon monoxide and hydrogen to pressurize the autoclave to 80 kg/cm$^2$.G. The reaction was carried out at a temperature of 90° C. and at a pressure of 80 to 85 kg/cm$^2$.G for 4 hours.

After cooling, the pressure was returned to atmospheric pressure, and the reaction mixture was recovered from the autoclave and distilled for purification to yield 396 g of the reaction product having a boiling point of 131° to 140° C. at 0.3 mmHg. The product consisted of two components:

(3)  5-(4,8-dimethyl-3,7-nonadienyl)-5-methyltetrahydro-2-furanol; and (4) 4-hydroxy-4,8,12-trimethyl-7,11-tridecadienal.

The ratio of the components (3) to (4) was 95:5.

The NMR spectra of the (3) and (4) had the following absorption characteristics (solvent: CDCl$_3$, TMS as the internal standard):

For both isomers (3) and (4):

δ=1.14 (s), δ=1.38 (s), δ=1.60 (bs), δ=1.68 (bs), δ=1.0-2.3 (m), δ=3.05 (m), δ=5.10 (m)

For isomer (3): δ=5.43 (m)

For isomer (4): δ=2.3-2.7 (m), δ=9.55 (m)

(s=singlet, bs=broad singlet, m=multiplet)

The infrared absorption spectra were observed at the following wavelength portions:

3400, 2960, 2915, 1720, 1445, 1375, 1103 and 830 cm$^{-1}$

The reaction product had distinctive fragrance similar to that of a mild and sweet flower.

EXAMPLE 5

A 100 ml Hastelloy C autoclave was charged with 10 g of nerolidol, 0.06 g of dicobalt octacarbonyl and 25 ml of toluene. The autoclave was then charged with equal volumes of a mixed gas of carbon monoxide and hydrogen to pressurize the autoclave to 100 kg/cm$^2$.G. The reaction was carried out at a temperature of 100° C. and a pressure of 100–110 kg/cm$^2$.G for 6 hours. After cooling, the pressure was returned to atmospheric pressure, and the reaction mixture was recovered from the autoclave and distilled for purification to yield 3.9 g of the reaction product having a boiling point of 140° to 160° C. at 0.5 mmHg. The product consisted of compounds (3) and (4) with a ratio of 92:3.

EXAMPLE 6

A perfume for use in the toilet preparation was provided in accordance with the following formulation:

|  | parts |
| --- | --- |
| Benzyl acetate | 100 |
| Benzyl alcohol | 100 |
| α-Amylcinnamic aldehyde | 150 |
| Phenethyl alcohol | 100 |
| β-Ionone | 100 |
| Jasmin absolute | 50 |
| Musk ambrette | 50 |
| Clarly saze oil | 30 |
| Patchouli oil | 20 |
| Compound (3) | 300 |
|  | 1,000 |

Addition of the compound (3) provided the perfume with the sweet smell of a natural flower.

While the invention has been described in detail and with reference to specific embodiments thereof, it will be apparent to one skilled in the art that various changes and modifications can be made therein without departing from the spirit and scope thereof.

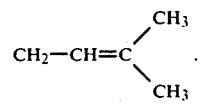

What is claimed is:

1. A tetrahydrofuranol compound of the general formula:

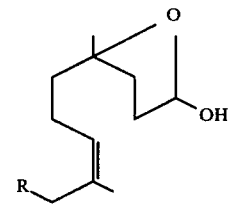

wherein R is H or

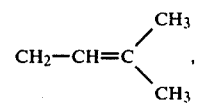

or a tautomer thereof.

2. The compound of claim 1, wherein R is H.

3. The compound of claim 1, wherein R is